United States Patent [19]

Adamson

[11] Patent Number: 5,499,982
[45] Date of Patent: Mar. 19, 1996

[54] SURGICAL PIN PROTECTOR

[76] Inventor: Paul H. Adamson, PSC 77 Box 4386, APO AP, 963

[21] Appl. No.: 128,465

[22] Filed: Sep. 28, 1993

[51] Int. Cl.⁶ .................................................. A61B 17/56
[52] U.S. Cl. ............................................ 606/53; 606/72
[58] Field of Search .................... 606/103, 53, 75, 606/62, 60, 59, 72, 86; 602/22, 30, 31

[56] References Cited

U.S. PATENT DOCUMENTS

| | | | |
|---|---|---|---|
| 237,949 | 2/1881 | Batcheller | 602/22 |
| 1,144,103 | 6/1915 | Brant | 602/22 |
| 1,229,633 | 6/1917 | Manning | 602/22 |
| 1,375,690 | 4/1921 | George | 602/22 X |
| 1,417,414 | 5/1922 | Sanders . | |
| 1,879,609 | 9/1932 | Hannon | 602/22 |
| 3,094,120 | 6/1963 | Blosser | 606/67 |
| 3,351,054 | 11/1967 | Florek | 606/62 |
| 3,832,997 | 9/1974 | Cappelletti | 602/11 |
| 4,414,964 | 11/1983 | Farino et al. | 602/30 |
| 4,813,406 | 3/1989 | Ogle, II | 602/22 |
| 4,969,909 | 11/1990 | Barouk | 606/62 |
| 5,031,608 | 7/1991 | Weinstein | 602/22 |
| 5,095,897 | 3/1992 | Clark et al. | 602/22 |
| 5,300,075 | 4/1994 | Gordon | 606/53 X |

FOREIGN PATENT DOCUMENTS 118722  3/1901  Germany ................................ 602/22

*Primary Examiner*—Tamara L. Graysay
*Attorney, Agent, or Firm*—Standley & Gilcrest

[57] ABSTRACT

A surgical pin protector placed on the tip of a patient's finger or toe for shielding the end of a surgical pin which protrudes from the tip of a patient's finger or toe, from external blows, including a protective cavity where the protruding end of the surgical pin is shielded.

1 Claim, 1 Drawing Sheet

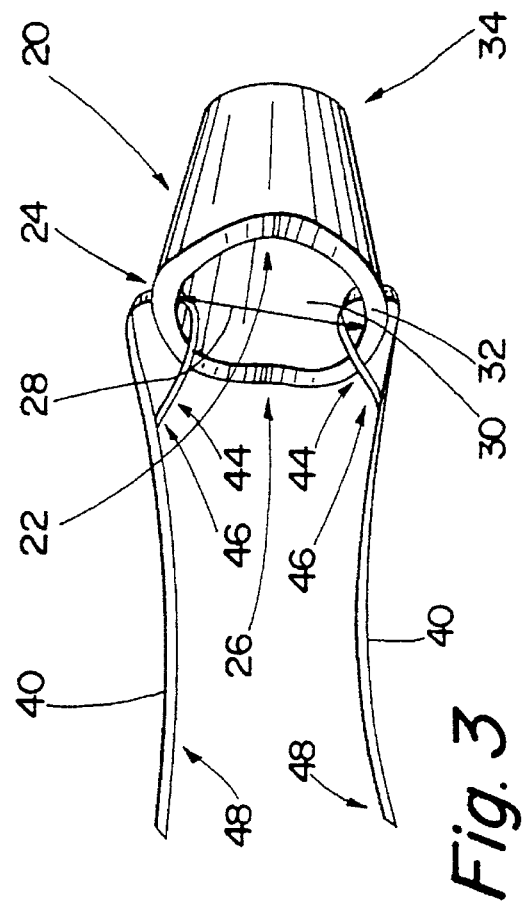
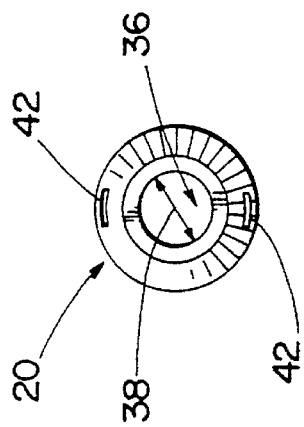
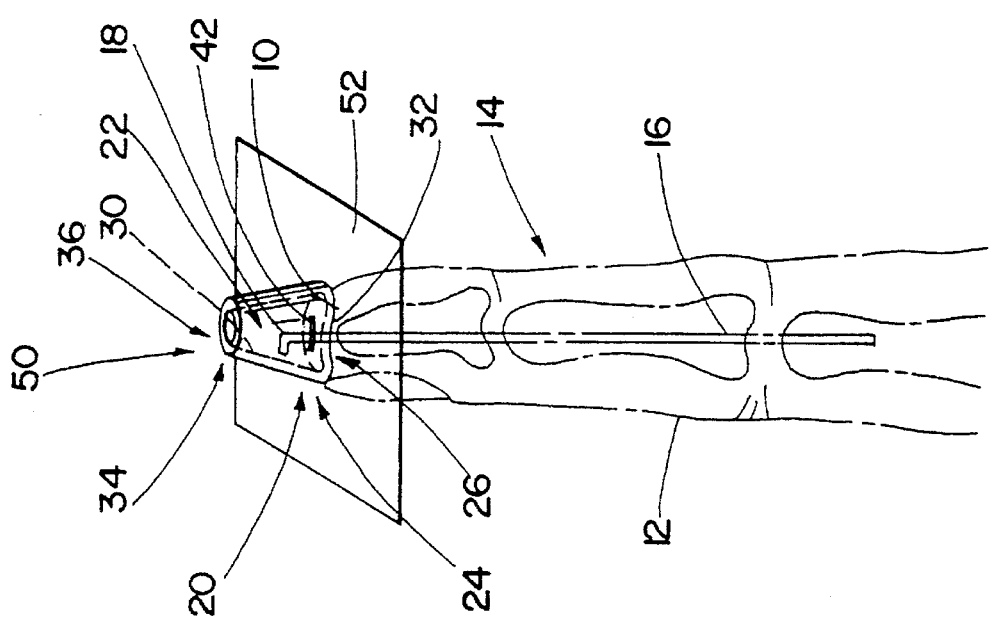

SURGICAL PIN PROTECTOR

BACKGROUND AND SUMMARY OF THE INVENTION

The present invention relates generally to protection of surgical pins which protrude from the skin, and more particularly, to protection of surgical pins which protrude from the skin during the period after orthopedic surgery has been performed.

During certain orthopedic operations, a steel surgical pin must be inserted through the bones to set the bones in the proper alignment. This surgical pin must remain in place for the period of time necessary for the bones to set properly. Since the surgical pin is not removed until after the healing period, one end of the pin typically extends out from the skin so that the pin can be readily removed once healing is accomplished. One problem with the pin protruding from the end of a finger or toe is that if the pin is bumped or jammed by an external object, it can cause severe discomfort to the patient.

A need exists for a device which shields the end of a surgical pin protruding from an injured finger or toe from any external blow, thus relieving the patient of unnecessary discomfort. The surgical pin protector of the present invention is capable of shielding the pin from an external blow which may be directed to the plane of the pin. The present invention is preferably capable of shielding an external blow so that the protruding end of the surgical pin remains undisturbed. To accomplish this, the present invention contains a protective cavity in which the protruding end of the surgical pin is located. This protective cavity is preferably of sufficient size such that the protruding end of the surgical pin is not in contact with the inner wall of the present invention.

The body of the present invention comprises a first end having an annular opening through which the protruding end of the surgical pin passes into the protective cavity. The body preferably has a shape that will disperse any applied force away from the surgical pin using the surrounding skin and soft tissues as the means of resisting a force applied to the protector body.

The body of the present invention further preferably includes a second end opposite the first end having an annular opening through which the protruding end of the surgical pin may pass temporarily if the present invention is subjected to a severe external blow. This feature prevents the protruding end of the surgical pin from coming into contact with the second end when the present invention is subjected to such a severe external blow. Furthermore, this annular opening in the second end can be used to view the protruding end of the surgical pin to ensure that the pin remains properly aligned. This annular opening also allows viewing of the surrounding skin for signs of sepsis or necrosis on application of such medicines that may be used in their prevention.

The body of the present invention is preferably flare-shaped with the first end having a larger diameter which tapers down to the second end having a smaller diameter. This flare-shaped feature allows the body of the present invention to be temporarily and partially forced down the shaft of the patient's finger or toe when it is subjected to a severe head-on blow. The flare-shape also allows the patient greater dexterity when so applied. The body of the present invention is preferably composed of a relatively hard rubber material which is capable of absorbing the impact of an external blow so that the impact of the external blow is not merely transferred to the skin and soft tissues surrounding the pin.

The present invention may also provide a means for fastening the body of the invention to the tip of the patient's finger or toe. In one embodiment of the present invention, two slits located near the rim of the first end and positioned 180° apart, allow for the attachment of two retaining strips to the body of the invention. These retaining strips may be secured to the body of the invention by inserting one end of one retaining strip through one slit and attaching this end to the remaining length of the retaining strip through the use of any suitable means such as gluing, stitching, riveting, or the like, and doing the same with the other strip and slit. After positioning the body of the present invention in the proper location on the tip of the patient's finger or toe, the remaining length of the two retaining strips may then be secured to the post-operative dressing which has been placed on the injured finger or toe along both sides of the shaft of the finger or toe. The body of the present invention could be positioned over a pin located in another place on the body and also secured to the post-operative dressing.

A primary object of the present invention is to provide a surgical pin protector of simple and low cost form which can be quickly, conveniently, and repeatedly applied to and detached from the tip of an injured finger or toe either by the patient himself or by another person.

Another object of the present invention is that it may be made in varying sizes so as to fit properly on the tips of fingers and toes of varying sizes.

Other principal features and advantages of the present invention will become apparent to those skilled in the art upon review of the following detailed description, claims, and drawings.

BRIEF DESCRIPTION OF THE DRAWINGS

FIG. 1 is a side view of the body of the invention located on an injured finger which illustrates the invention's position relative to the fingertip and to the protruding end of the surgical pin;

FIG. 2 is an end view of the body of the invention standing alone; and

FIG. 3 is a perspective view of the body of the invention which illustrates a means for attaching the body of the invention to the fingertip.

DESCRIPTION OF PREFERRED EMBODIMENT(S)

Referring now to the drawings, and particularly FIG. 1, there is illustrated the body 20 of the surgical pin protector located on the tip 10 of a patient's injured finger 12, in which a steel surgical pin 16 has been placed. The protruding end 18 of the surgical pin 16 is located in the protective cavity 22. An end view of the body 20 of the surgical pin protector standing alone is shown in FIG. 2. A perspective view of the surgical pin protector which includes an embodiment of a means for attaching the body 20 of the invention to the tip of a finger or toe is shown in FIG. 3.

The protective cavity 22 in which the protruding end 18 of the surgical pin 16 is located is preferably of sufficient size such that the protruding end 18 is not in contact with the inner wall 30.

The body 20 includes a first end 24 having a first or larger annular opening 26 which is illustrated in FIG. 3. This larger annular opening 26 is preferably of sufficient size such that the protruding end 18 of the surgical pin 16 can readily pass through the inner diameter 28 of this opening without making contact with the inner wall 30 of the body 20. This larger annular opening 26 and the bottom surface 32 of the first end 24 are contoured to ensure a relatively snug fit on the tip 10 of the patient's finger 12 or of such diameter so as to evenly distribute forces if applied over other body areas (now shown).

The body 20 also includes a second end 34 having a second or smaller annular opening 36. This smaller annular opening 36 is preferably of sufficient size such that the protruding end 18 of the surgical pin 16 may pass partially through the inner diameter 38 of this opening if the body 20 is subjected to a severe external blow in a direction 50 perpendicular to an imaginary plane 52. This prevents the protruding end 18 of the surgical pin 16 from coming into contact with the second end 34 of the body 20 when the body 20 is forced onto the digit 12, resulting in the body 20 compressing and/or moving slightly further down the shaft of the digit 12, or compressing the surrounding soft tissue if installed elsewhere on the body. Furthermore, this second smaller annular opening 36 in the second end 34 may be used to observe the protruding end 18 of the surgical pin 16 to ensure that the protruding end 18 is properly aligned and to ensure that the skin at the tip 10 of the finger 12 remains uninfected.

The body 20 is preferably flare-shaped with the first end 24 having a larger inner diameter 28 which tapers down to the second end 34 having a smaller inner diameter 38, thus allowing the body 20 to be temporarily forced down the shaft 14 of the patient's finger 12 when the body 20 is subjected to a severe external blow. The body 20 is preferably constructed of a relatively hard rubber which is capable of absorbing the impact of an external blow so that the impact of the blow is not merely transferred to the tip 10 of the patient's finger 12 or to the protruding end 18 of the surgical pin.

In one embodiment of the present invention, the body 20 may be fastened to the tip 10 of the patient's finger 12 by the use of two retaining strips 40. These retaining strips 40 may be attached to the body 20 by the use of two slits 42 located near the rim of the first end 24 and positioned 180° apart from one another as illustrated in FIG. 2. These two strips 40 may be secured to the body 20 by inserting the first ends 44 of a strip through a respective slit 42 and attaching the first end 44 to the strip 40 through the use of any suitable means such as gluing, stitching, or riveting at points 46. After positioning the body 20 in the proper location on the tip 10 of the patient's finger 12, the remaining lengths 48 of the two strips 40 may then be secured to the post-operative dressing (not shown) which has been placed on the injured finger 12 along both sides of the shaft 14 of the patient's injured finger 12. The material for the strips 40 may be VELCRO®, or other suitable material that can be taped to the shaft 14 or secured to the shaft 14 in other suitable ways that would be apparent to one skilled in the art.

In another embodiment of the present invention, the means for fastening the body of the invention to the tip of the patient's finger or toe makes use of two strips of post-operative tape which are similarly secured to the body of the invention but are secured directly to the skin on both sides of the shaft of the injured finger or toe.

The aforementioned means for fastening the body of the invention to the tip of the patient's finger or toe may be more securely accomplished by using four strips, instead of two strips. Tape may be used to wrap the strips securely to the patient's injured finger or toe. This will help to prevent an external blow in any direction from dislodging the body of the present invention from the tip of the injured finger or toe.

In another embodiment of the present invention, the first end of the body is extended so that the first end proceeds slightly down the shaft of the finger or toe in order that post-operative tape can be applied circumferentially down the shaft of the injured finger or toe to secure the body of the present invention to the. Various other securing means can also be employed to fasten or otherwise hold the present invention to the tip of the patient's injured finger or toe.

The above-described features of the preferred embodiments are not to be construed as limiting the scope of the invention. The invention can be applied to protect pins other than those that project from a finger or toe, such as from an injured wrist or foot. The claims herein are not limited by specific features but instead are open to a wider interpretation that would encompass certain modifications to the invention.

What is claimed is:

1. A surgical pin protector for shielding the end of a surgical pin which protrudes from the end of a patient's injured finger or toe comprising:

a flare-shaped body which contains a protective cavity which is adapted to shield said protruding end of said surgical pin; said body including a first end having a first annular opening with an inner diameter of sufficient size so that said protruding end of said surgical pin may enter said protective cavity; said first end having a bottom surface which together with said first annular opening is contoured to said end of said patient's injured finger or toe enabling said body to fit on said end of said finger or toe; said body including a second end having a second annular opening with an inner diameter of sufficient size so that said protruding end of said surgical pin may pass through temporarily if said body is subjected to a severe external force; and two retaining strips, each of said strips engaged within respective slits in said body.

* * * * *